(12) United States Patent
Pflanz et al.

(10) Patent No.: US 9,156,594 B2
(45) Date of Patent: Oct. 13, 2015

(54) CLOSURE FOR A NUTRIENT MEDIUM CONTAINER

(75) Inventors: Karl Pflanz, Gleichen (DE); Andreas Graus, Noerten-Hardenberg (DE)

(73) Assignee: Sartorius Stedim Biotech GmbH (DE)

( * ) Notice: Subject to any disclaimer, the term of this patent is extended or adjusted under 35 U.S.C. 154(b) by 0 days.

(21) Appl. No.: 13/817,058

(22) PCT Filed: Oct. 4, 2011

(86) PCT No.: PCT/EP2011/004923
§ 371 (c)(1),
(2), (4) Date: Feb. 14, 2013

(87) PCT Pub. No.: WO2012/069106
PCT Pub. Date: May 31, 2012

(65) Prior Publication Data
US 2013/0175275 A1    Jul. 11, 2013

(30) Foreign Application Priority Data

Nov. 23, 2010    (DE) .......................... 10 2010 052 030

(51) Int. Cl.
*B65D 41/06*    (2006.01)
*B65D 41/04*    (2006.01)
(Continued)

(52) U.S. Cl.
CPC ................. *B65D 41/04* (2013.01); *B01L 3/508* (2013.01); *B65D 41/06* (2013.01);
(Continued)

(58) Field of Classification Search
CPC ...... B65D 41/06; B65D 41/065; B65D 41/04; B65D 43/0225; B65D 2313/04; B65D 50/061; C12M 23/10; C12M 23/38; C12M 23/46; B01L 2200/025; B01L 2300/042

USPC .......................... 220/293, 298; 215/222, 332
See application file for complete search history.

(56) References Cited

U.S. PATENT DOCUMENTS

| 3,158,553 A | 11/1964 | Carski |
|---|---|---|
| 3,339,770 A | 9/1967 | Weigand |

(Continued)

FOREIGN PATENT DOCUMENTS

| CN | 101843998 A | 9/2010 |
|---|---|---|
| DE | 1 940 202 | 6/1966 |

(Continued)

OTHER PUBLICATIONS

German Office Action of Nov. 10, 2011.
(Continued)

*Primary Examiner* — Fenn Mathew
*Assistant Examiner* — James N Smalley
(74) *Attorney, Agent, or Firm* — Gerald E. Hespos; Michael J. Porco; Matthew T. Hespos

(57) ABSTRACT

The invention relates to closure, in particular for a nutrient medium container, wherein a lower part can be covered by an upper part, wherein the lower part and the upper part can be locked against each other by means of at least one locking receptacle and at least one locking part by rotating the lower part and the upper part about a longitudinal axis, and wherein the locking receptacle has a receptacle groove that is covered by a shoulder and that extends perpendicularly to the longitudinal axis, in which receptacle groove the locking part engages, wherein the shoulder has at least one ramp surface extending at an angle from the longitudinal axis on the outer face of the shoulder facing away from the receptacle groove.

9 Claims, 3 Drawing Sheets

(51) Int. Cl.
  *C12M 3/00* (2006.01)
  *B65D 43/06* (2006.01)
  *B65D 43/02* (2006.01)
  *B01L 3/00* (2006.01)
  *C12M 1/22* (2006.01)
  *C12M 1/00* (2006.01)

(52) U.S. Cl.
  CPC ........... *B65D 43/0231* (2013.01); *B65D 43/06* (2013.01); *C12M 23/10* (2013.01); *C12M 23/38* (2013.01); *C12M 23/46* (2013.01); *B01L 2200/025* (2013.01); *B01L 2300/042* (2013.01)

(56) References Cited

U.S. PATENT DOCUMENTS

| | | | |
|---|---|---|---|
| 3,474,004 | A | 10/1969 | Fink |
| 3,667,636 | A * | 6/1972 | Landen .................. 215/214 |
| 5,348,885 | A * | 9/1994 | Labarthe .................. 435/305.4 |
| 6,969,606 | B2 | 11/2005 | Minton |
| 6,969,607 | B2 | 11/2005 | Minton |
| 2005/0089997 | A1* | 4/2005 | Minton .................. 435/288.3 |
| 2006/0240549 | A1 | 10/2006 | Minton |
| 2010/0032403 | A1* | 2/2010 | Hajichristou et al. ........ 215/337 |
| 2013/0101479 | A1* | 4/2013 | Huet et al. .................. 422/551 |

FOREIGN PATENT DOCUMENTS

| | | |
|---|---|---|
| DE | 10 2007 027 273 | 11/2008 |
| EP | 0 171 174 | 2/1986 |

OTHER PUBLICATIONS

International Search Report of Dec. 28, 2011.

Translation International Preliminary Report on Patentability.

* cited by examiner

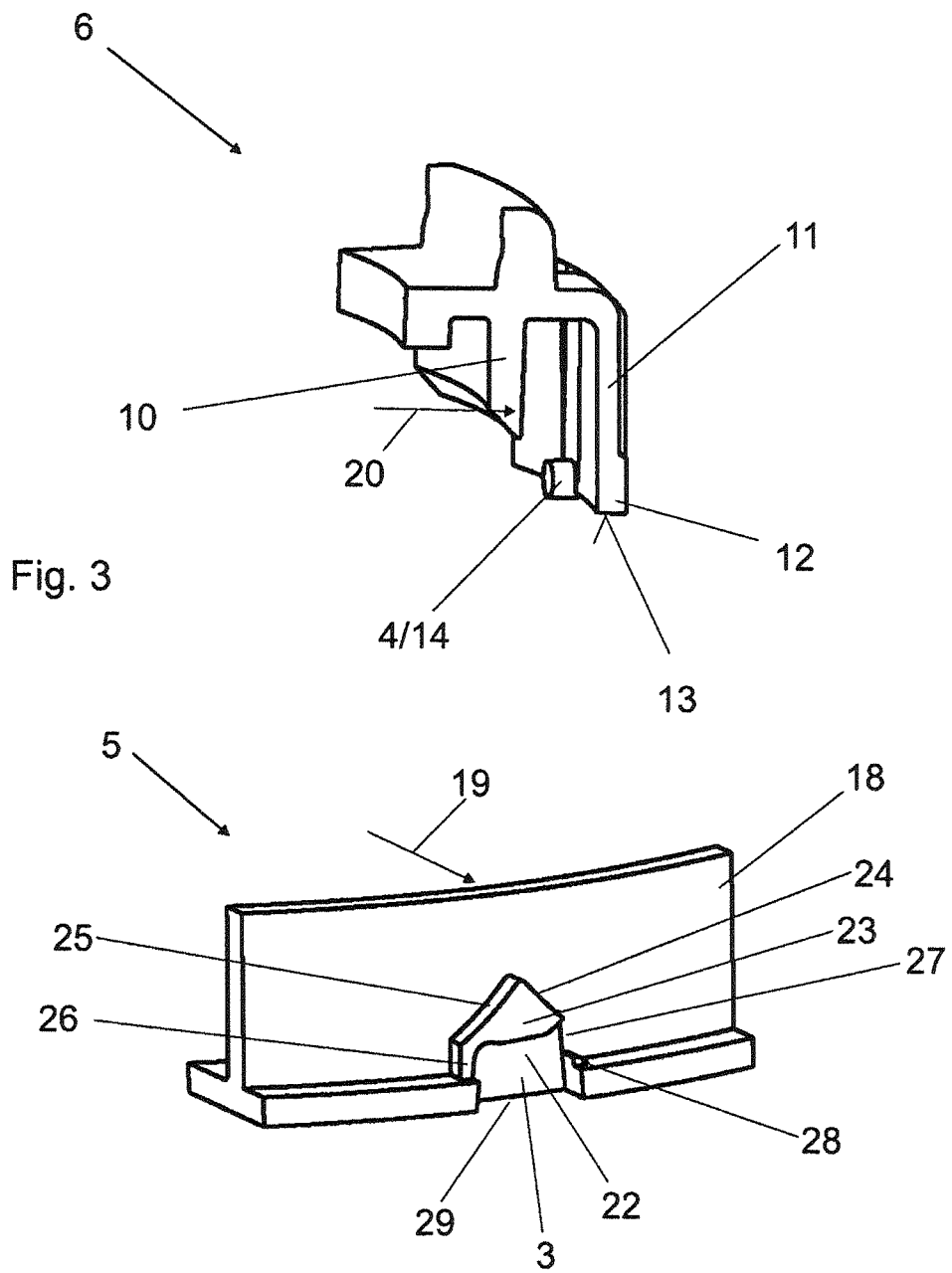

CLOSURE FOR A NUTRIENT MEDIUM CONTAINER

BACKGROUND OF THE INVENTION

1. Field of the Invention

The invention relates to closure, in particular for a nutrient medium container, wherein a lower part can be covered by an upper part, wherein the lower part and the upper part can be locked against each other by means of at least one locking receptacle and at least one locking part by rotating the lower part and the upper part about a longitudinal axis, and wherein the locking receptacle has a receptacle groove that is covered by a shoulder and that extends perpendicularly to the longitudinal axis, in which receptacle groove the locking part engages.

2. Description of the Related Art

A closure for a nutrient medium container, wherein a lower part can be covered by an upper part, is known from DE 10 2007 027 273 A1. The lower part and the upper part can be locked against each other through two or more locking receptacles and two or more locking parts by rotating them about a longitudinal axis. To do so, the locking receptacle has a receptacle groove that is covered by a shoulder and that extends perpendicularly to the longitudinal axis, in which receptacle groove the locking part engages.

The disadvantage of this is that when used in automatic systems in which the upper part is automatically positioned on and/or removed from the lower part, for instance by a robot arm, an undesirable error rate occurs due to incorrect positioning when the locking part comes in contact with the shoulders of the locking receptacle during positioning.

The same disadvantages occur with regard to the closures known from US 2006/0240549 A1, U.S. Pat. No. 6,969,606 B2 and U.S. Pat. No. 6,969,607 B2. These documents also disclose nutrient medium containers or "petri dishes" in which a lower part has a locking receptacle with a shoulder oriented perpendicularly to the longitudinal and/or rotational axis, which shoulder covers a locking part of an upper part and/or lid when in the locked state.

These known closures also lead to undesirable positioning problems in automatic systems.

The task of the present invention is therefore to design the known closures and/or locking systems, especially for nutrient medium containers, such that the frequency of incorrect positioning is reduced or eliminated entirely when the upper part is automatically positioned on the lower part.

SUMMARY OF THE INVENTION

This task is solved in connection with the generic part of Claim 1 in that the shoulder has at least one ramp surface extending at an angle from the longitudinal axis on the outer face of the shoulder facing away from the receptacle groove.

When the locking part comes in contact with the shoulder of the locking receptacle, the upper and lower part rotate against each other on account of the shoulder and its ramp surface extending at an angle to one side such that incorrect positioning is reliably avoided.

In accordance with a preferred embodiment of the invention, the outer face of the shoulder comprises two ramp surfaces extending at an angle from the longitudinal axis, which surfaces meet to form a triangle shape.

Assuming the same shoulder width, the triangular shoulder reduces by half the torsional angle of the upper part with respect to the lower part.

In another preferred embodiment of the invention, the receptacle groove of the locking receptacle has at its end a contact surface for the locking part. This ensures that the lower part and upper part always interlock in the same locking position.

In accordance with another preferred embodiment of the invention, the end of the receptacle groove opposite the contact surface is bordered by a groove inlet, which is defined by the beginning of the shoulder, wherein a threshold that the locking part must pass is arranged anterior to the groove inlet.

Such a threshold has the advantage of ensuring that the upper part cannot interlock with the lower part accidentally, but only as a result of intentional application of force. The threshold is preferably designed as a quarter-cylinder or half-cylinder placed in an anterior position to the groove.

It is especially undesirable for the upper part to interlock accidentally with the lower part as a result of incorrect positioning by a robot arm when a multitude of upper and lower parts are placed loose and in pairs on a running conveyor belt. In this case, after accidental interlocking of the upper part with the lower part and before the lower part is filled with a medium, especially a nutrient medium, the robot arm would not only lift the upper part away from the lower part for subsequent filling with the medium, as desired, but would also lift the entire container, consisting of the interlocked upper and lower part, off of the conveyor belt. The nutrient medium would then contaminate the running conveyor belt, as it would not be dispensed into the lower part, but onto the conveyor belt itself, which is undesirable.

This advantage of avoiding accidental interlocking of the upper part with the lower part can be realized very reliably when the threshold to the groove inlet that the locking part must pass is implemented in combination with the two ramp surfaces extending at an angle from the outer face of the shoulder of the locking receptacle and which meet to form a triangle; this is because when the robot arm places the upper part on the lower part, the probability is about equal that the locking part will be set down on one of the two triangular ramp surfaces and will come to rest to the left or right of the receptacle groove without interlocking with the receptacle groove.

In accordance with another preferred embodiment of the invention, the locking receptacle is arranged on the lower part and the locking part is arranged on the upper part. In principle it is also possible to arrange the locking receptacle on the upper part and the locking part on the lower part.

In accordance with another preferred embodiment of the invention, the locking receptacle is arranged on the outside of an exterior wall of the lower part adjacent to the base of the lower part, in a radial direction, the receptacle groove being open in a radial direction to the exterior.

Accordingly, the locking part is arranged in a radial inward direction on one of the exterior walls of the upper part that extends beyond the exterior wall of the lower part. The locking part is arranged adjacent to a free front face of the exterior upper part wall, which face is oriented away from a lid of the upper part.

According to another preferred embodiment of the invention, the locking part is designed as a locking pin which is made to fit the receptacle groove. The circular shape of the locking pin allows low-friction gliding of the contact surfaces.

In accordance with another preferred embodiment of the invention, the lower part and the upper part can be interlocked by way of two or more locking receptacles and locking parts arranged equidistant from one another. In accordance with the invention, the frequency of incorrect positioning is no longer dependent on the number of locking receptacles.

The locking receptacles and locking parts arranged equidistantly along the perimeter of the walls allow the parts to be fixed evenly to one another.

Further details regarding the invention can be obtained from the following detailed description and from the attached drawings, in which examples of preferred embodiments of the invention are depicted.

BRIEF DESCRIPTION OF THE DRAWINGS

FIG. 3 is a magnified spatial representation of an area near the locking part on the upper part in FIG. 1.

FIG. 4 is a magnified spatial representation of an area near the locking receptacle on the lower part in FIG. 1.

DETAILED DESCRIPTION OF THE PREFERRED EMBODIMENTS

Figure 1:
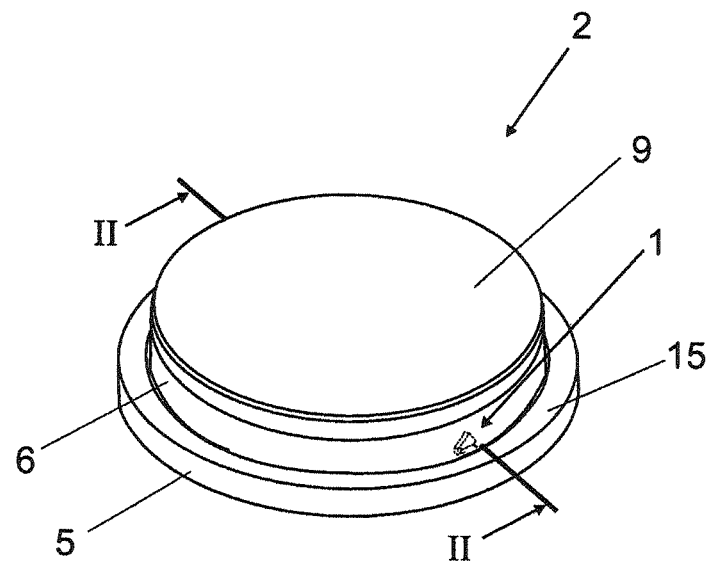
FIG. 1 is a spatial representation of a nutrient medium container with a closure drawn in dotted lines.
Figure 2:
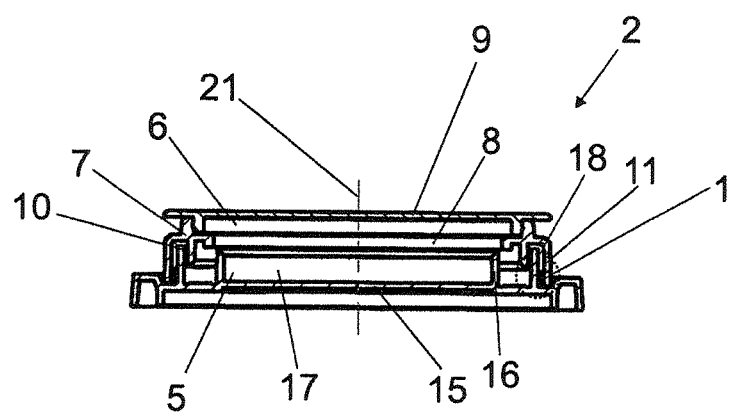
FIG. 2 is a lateral cross section of the nutrient medium container in FIG. 1, cut along the line II-II.
Figure 5:
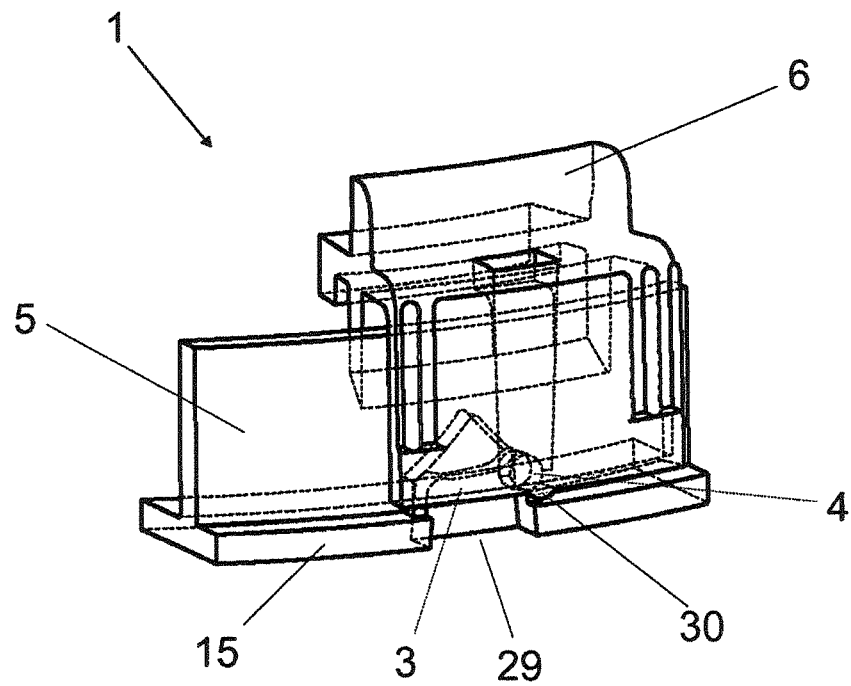
FIG. 5 is a spatial representation of the lower part in FIG. 4 with the upper part in FIG. 3 positioned on it, but not interlocked.
Figure 6:
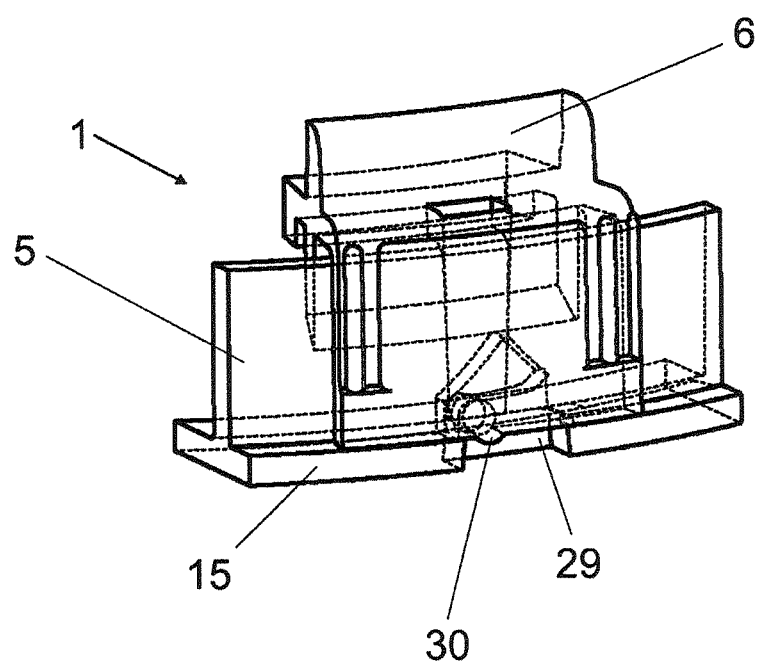
FIG. 6 is a spatial representation of an area of the upper part and lower part in FIG. 5, in the interlocked position.

A closure 1 of a nutrient medium container 2 essentially consists of a locking receptacle 3 and a locking part 4.

The nutrient medium container 2 consists of a lower part 5 and an upper part 6. The upper part 6 in the exemplary embodiment is composed of two parts and consists of a connection ring 7 whose upper opening 8 is closed by a lid 9 via a compression joint. The upper part 6 has a ring-shaped collar 10 that is oriented away from the lid 9, which collar is surrounded at a distance by an exterior upper part wall 11. The free end 12 of the upper part wall 11 that is turned away from the lid 9 has a front face 13. Two locking parts 4 that are oriented radially inward and adjacent to the front face 13 and across from one another are arranged at the free end 12 of the exterior upper part wall 11 and are designed as locking pins 14.

The lower part 5 has a base 15 with a ring-shaped interior wall 16 which encloses a dish space 17 to accommodate media, especially nutrient media for microbiology. Arranged coaxially to the interior wall 16, the lower part 5 comprises an exterior wall 18 whose interior diameter 19 is dimensioned to fit the exterior diameter 20 of the collar 10 of the upper part 6. The upper part 6 is thus guided by its exterior diameter 20 of the collar 10 in the interior diameter 19 of the exterior wall 18 of the lower part 5. The exterior wall 11 of the upper part 6 with its locking pins 14 extends beyond the exterior wall 18 of the lower part 5. The locking receptacle 3 is arranged adjacent to the base 15 on the exterior wall 18 of the lower part 5. The locking receptacle 3 has a receptacle groove 22 arranged perpendicular to the longitudinal axis 21 which is arranged orthogonally and medially with respect to the base 15. The receptacle groove 22 has in the direction of the upper part 6 a shoulder 23 that covers or limits the receptacle groove 22. On its exterior face oriented away from the receptacle groove 22, the shoulder 23 comprises two ramp surfaces 24, 25 that extend at an angle to the longitudinal axis 21 and which meet to form a triangle. The receptacle groove 22 is bordered at one end by a contact surface 26 which extends between the base 15 and the shoulder 23. At the end opposite from the contact surface 26, the receptacle groove 22 has a groove inlet 27. A threshold 28 is arranged anterior to the groove inlet 27. In the exemplary embodiment, the threshold 28 is realized as a quarter-cylinder. The threshold 28 can also be realized as a half-cylinder or any other shape that provides resistance which must be overcome by the locking pin 14 to introduce and remove the locking pin 14 into/from the receptacle groove 22.

The receptacle groove 22 has a corresponding extension above the threshold 28.

The receptacle groove 22 transitions into a base cutout 29 in the direction of the base 15. When in the locked state, a cylinder section of the locking pin 14, which extends beyond the front face 13 of the exterior wall 11 of the upper part, can protrude into the base cutout.

The upper parts 6 can be automatically controlled so as to be positioned on top of the lower part 5 by a robot and/or handling unit. To the extent that the locking part 4 comes in contact with the shoulder 23 during positioning, the locking pin 14 touches on one of the ramp surfaces 24, 25 whereupon the parts 5, 6 rotate against one another such that the locking pin 14 touches the base 15 laterally, next to the shoulder 23 or the locking receptacle 3.

Accordingly, the upper part can simply be removed by a handling element. After the filling of the nutrient medium container 2, rotation around the longitudinal axis 21 of the upper part 6 with respect to the lower part 5 results in the locking pin 14 being moved across the threshold 28, through the groove inlet 27, and into the receptacle groove 22.

Of course, the embodiments discussed in the specific description and shown in the Figures are merely illustrative exemplary embodiments of the present invention. In the light of this disclosure a person skilled in the art is given a wide range of possible variations.

The invention claimed is:

1. A nutrient medium container, comprising:
a lower part (5) having a base (15) and a wall (18) projecting up from the base (15) at a position spaced inward from an outer periphery of the base (15), a shoulder (23) projecting out on an outer surface of the wall (18) at a position spaced up from the base (15), the shoulder (23) having two ramp surfaces (24, 25) aligned to the base (15) at acute angles and meeting at an angle, the shoulder (23) further having a lower surface facing away from the ramp surfaces (24, 25) to form a triangle shape, a contact surface (26) extending from the base (15) to the lower surface of the shoulder (23), a receptacle groove (22) extending circumferentially from the contact surface (26) along the lower surface of the shoulder (23) and defining a groove inlet (27) opposite the contact surface (26), the groove inlet (27) extending from the lower surface of the shoulder (23) to a position substantially aligned with the base (15), a threshold (28) projecting on the lower part (5) at the groove inlet (27); and
an upper part (6) with an exterior wall (11) dimensioned to telescope over the wall (18) of the lower part (5), at least one locking part (4) projecting in from the exterior wall (11) at a position in proximity to a lower end of the exterior wall (11), the locking part (4) being dimensioned to enter the groove inlet (27) by rotating at least one of the upper part (6) and the lower part (5) relative to one another when the exterior wall (11) of the upper part (6) is telescoped to a position substantially adjacent the base (15) of the lower part (5), wherein the ramp surfaces (24, 25) guide the locking part (4) from the shoulder (23) toward the base (15) and wherein the threshold (28) must be passed by the locking part (4) for entry of the locking part (4) into the receptacle groove (28).

2. The nutrient medium container of claim 1, wherein the threshold (28) is arranged in an anterior position as a quarter-cylinder or half-cylinder and has a convex arcuate surface facing away from the groove (22).

3. The nutrient medium container of claim 2, wherein, the locking receptacle (3) is arranged adjacent to the base (15) of the lower part (5) in a radial direction on the outside of the wall (18) of the lower part (5) and the groove (22) is open in a radial direction to the exterior.

4. The nutrient medium container of claim 3, wherein, the locking part (4) is a locking pin (14) that is made to fit the groove (22).

5. The nutrient medium container of claim 4, wherein, the lower part (5) and the upper part (6) can be locked against each other via two or more locking receptacles (3) and locking parts (4) arranged equidistantly with respect to one another.

6. The nutrient medium container of claim 1, wherein, the locking receptacle (3) is arranged adjacent to the base (15) of the lower part (5), in a radial direction on the outside on an exterior wall (18) of the lower part (5) and that the receptacle groove (22) is open in a radial direction to the exterior.

7. The nutrient medium container of claim 1, wherein, the locking part (4) is adjacent to a free front face (13) of the exterior wall (11) that faces away from a lid (9) of the upper part (6).

8. The nutrient medium container of claim 1, wherein the locking part (4) is a locking pin (14) that is made to fit the receptacle groove (22).

9. The nutrient medium container of claim 1, wherein, the lower part (5) and the upper part (6) can be locked against each other via two or more locking receptacles (3) and locking parts (4) arranged equidistantly with respect to one another.

\* \* \* \* \*